United States Patent
Preston et al.

(12)

(10) Patent No.: US 6,274,087 B1
(45) Date of Patent: *Aug. 14, 2001

(54) BLOOD CELL ANALYZER WITH TUBE HOLDER AND CAP PIERCER

(75) Inventors: Charles R. Preston, Quakertown; Peter A. Bourdelle, Allentown Lehigh, both of PA (US)

(73) Assignee: BioChem Immunosystems Inc., Allentown, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/257,857

(22) Filed: Feb. 25, 1999

Related U.S. Application Data (63) Continuation of application No. 09/029,905, filed as application No. PCT/US97/00645 on Nov. 14, 1997, now Pat. No. 6,126,903.
(60) Provisional application No. 60/030,841, filed on Nov. 15, 1996.

(51) Int. Cl.[7] ............................. B01L 3/02; G01N 1/14; G01N 35/10
(52) U.S. Cl. ................. 422/100; 422/99; 422/104; 422/81; 422/63; 436/54; 436/180; 73/864.24; 73/864.25; 73/863.02; 73/863.03; 73/863.85
(58) Field of Search .................. 422/100, 99, 104, 422/81, 63; 436/54, 180; 73/864.24, 864.25, 863.02, 863.03, 863.85

(56) References Cited

U.S. PATENT DOCUMENTS

| | | | |
|---|---|---|---|
| 3,991,627 | * 11/1976 | Larid et al. | 73/423 R |
| 4,387,076 | 6/1983 | Cabrera et al. | 422/67 |
| 4,478,095 | 10/1984 | Bradley et al. | 73/864 |
| 4,713,218 | * 12/1987 | Schwartz | 422/99 |
| 4,861,553 | * 8/1989 | Mawhirt et al. | 422/65 |
| 4,928,539 | 5/1990 | Champseix et al. | 73/864 |
| 4,951,512 | 8/1990 | Mazza et al. | 73/861.23 |
| 4,962,041 | * 10/1990 | Roginski | 436/150 |
| 5,045,286 | * 9/1991 | Kiajima et al. | 422/100 |
| 5,240,679 | 8/1993 | Stettler | 422/67 |
| 5,413,000 | 5/1995 | Stark et al. | 73/864 |
| 5,455,007 | 10/1995 | Calvo et al. | 422/100 |
| 5,483,843 | 1/1996 | Miller et al. | 73/864 |
| 5,517,867 | 5/1996 | Ely et al. | 73/863 |
| 5,728,954 | * 3/1998 | Uffenheimer | 73/864.22 |

* cited by examiner

*Primary Examiner*—Long V. Le
*Assistant Examiner*—Kathryn Bex
(74) *Attorney, Agent, or Firm*—Seidel Gonda Lavorgna & Monaco, PC (57) ABSTRACT

The invention relates to a diagnostic medical device, and in particular to a blood cell analyzer which by manual or automatic operation withdraws and analyzes a minimal amount of blood that is stored in open or sealed vials. The analyzer includes a manually operated self cleaning sampling device for open vials and an automated self cleaning sampling device for sealed vials fitted with a pierceable cap.

6 Claims, 10 Drawing Sheets

BLOOD CELL ANALYZER WITH TUBE HOLDER AND CAP PIERCER

This application is a continuation of Ser. No. 09/029,905, filed Apr. 23, 1998, now U.S. Pat. No. 6,126,903, which is a 371 of PCT/US97/00645 filed Nov. 14, 1997, and claims benefit of provisional application 60/030,841, filed Nov. 15, 1996.

FIELD OF THE INVENTION

The invention relates to a diagnostic medical device, and in particular to a blood cell analyzer which by manual or automatic operation withdraws and analyzes a minimal amount of blood that is stored in open or sealed vials with pierceable caps.

BACKGROUND OF THE INVENTION

Blood sample analysis systems are known in which the operator must position and hold in place tubes or vials of the samples to be analyzed. The systems include needles which pierce a closure on a sample tube to provide communication between blood in the sample tube and the system. Such prior art systems expose operators to the risk of contamination and infection from blood samples, as well as the risk of being cut by broken glass or other shattered materials. In addition, the prior art systems can only accept a limited number of sizes of tubes or vials.

It is desired to have a safer, more flexible means for positioning and holding blood sample tubes and vials during the cap piercing operation. Specifically, it is desired to have a holding and piercing apparatus which is "hands off" during the piercing operation, so as to prevent exposure of the operator to contamination from the blood in the vial being penetrated. It is also desired to improve the safety of such an apparatus by incorporating a safety interlock system. It is also desired to make it easier to insert and remove tubes or vials from the holder. It also is desired to have more flexibility to analyze samples from many sizes of vials or tubes (e.g., from 10.25×64 mm to 16×100 mm).

SUMMARY OF THE INVENTION

The present invention is a blood cell analyzer which by manual or automatic operation withdraws and analyzes a minimal amount of blood that is stored in open or sealed vials. The analyzer includes a manually operated self cleaning sampling device for open vials and an automated self cleaning sampling device for sealed vials fitted with a pierceable cap. The analyzer further includes a red blood cell counter, white blood cell counter, hemoglobin detector, valving system, and electronic controller. The blood cell analyzer further includes features for precisely measuring and mixing whole blood or prediluted blood with diluent as needed in order to analyze the blood sample The present invention includes an apparatus for holding vials of varying sizes sealed with pierceable caps and for piercing the caps of the vials. The apparatus comprises a frame, holder, plate, cup, needle, driver, and an interlocking safety switch.

The frame has upper and lower ends. The holder is adjustably mounted on the upper end of the frame and is adapted to receive and hold the outer surface of a vial opposite the pierceable cap which seals the vial. The plate, which has an aperture in it, is mounted on the frame below the holder.

A cup is mounted on the top of the plate. The bottom of the cup has an aperture aligned with the aperture in the plate. The cup is adapted to receive the pierceable cap which seals the vial.

The needle is adapted to pierce the pierceable cap of the vial and to communicate with the contents of the vial. The needle is extendable and retractable through the apertures in the plate and the cup.

A driver, such as an electric motor, which extends and retracts the needle, is interlocked with the holder by a safety switch. The driver cannot extend the needle through the aperture in the cup whenever a vial is not held by the holder.

The apparatus may also include a needle cartridge assembly below the plate. The needle cartridge assembly has a lower end, a body, and an upper end, the top of which has an aperture aligned with the aperture in the plate. The body of the needle cartridge assembly contains the needle and a biasing means for engaging the needle and biasing the needle away from the pierceable cap of the vial. The biasing means may be a compression spring, such as a coil spring.

The apparatus may also include a rinse system for cleaning the needle. The needle cartridge assembly is connected to a rinse passage for selectively communicating a rinse fluid to the needle. The needle may be contained in a chamber within the needle cartridge assembly. The chamber is connected to the rinse passage, through which the rinse fluid is injected in one direction into the chamber, and from which the rinse fluid is withdrawn in another direction.

BRIEF DESCRIPTION OF THE DRAWINGS

For a better understanding of the present invention, reference is made to the accompanying drawings. The drawings show one embodiment of the invention as presently preferred. However, it should be understood that the invention is not limited to the precise arrangements and instrumentality shown in the drawings.

DETAILED DESCRIPTION OF THE INVENTION

Figure 1:
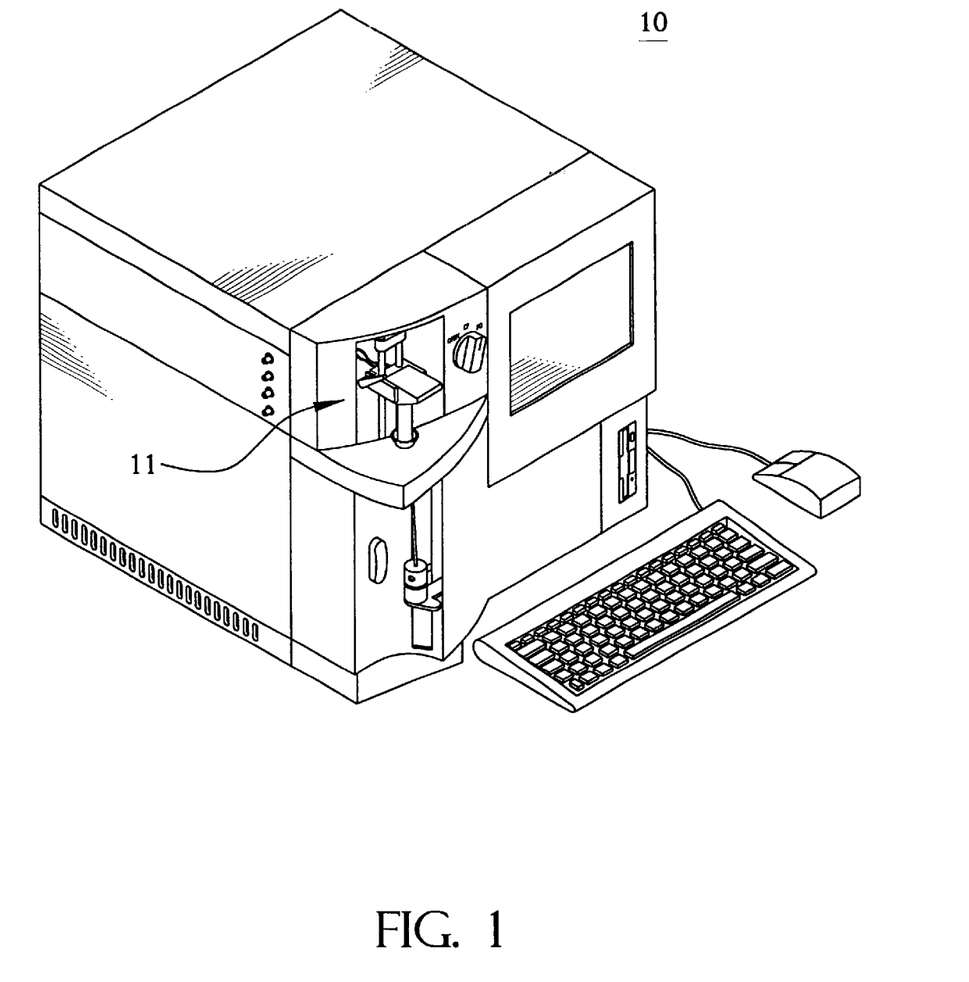
FIG. 1 shows a front view of blood cell analyzer having a vial holder and cap piercer device according to the present invention.

Referring to the drawings, where like elements are identified by like numerals, there is shown in FIG. 1 a blood cell analyzer 10 having a vial holder and cap piercer device 11 according to a preferred embodiment of the present invention.

Figure 2:
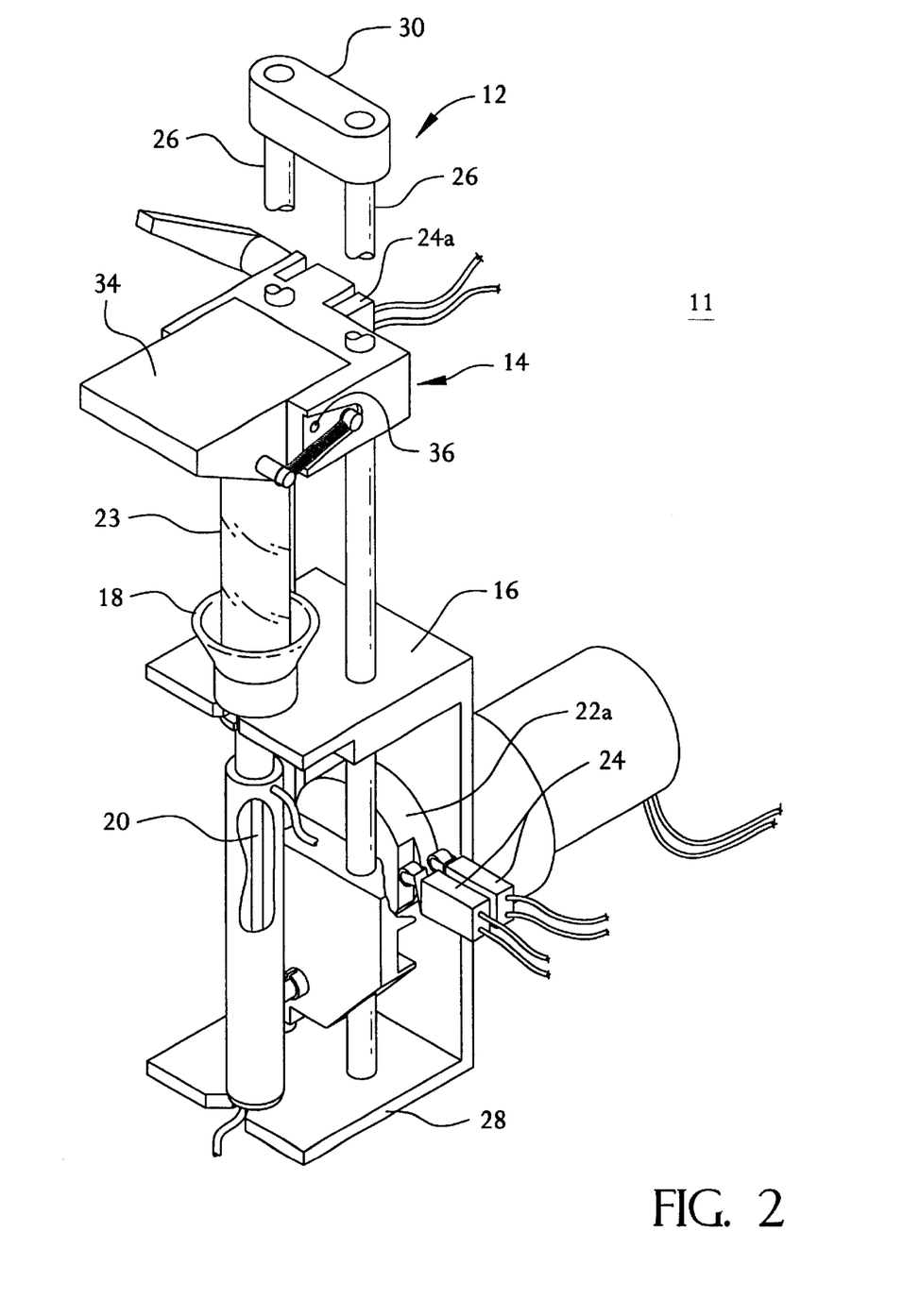
FIG. 2 is an isometric view of a vial holder and cap piercer according to the present invention.

FIG. 2 shows a preferred embodiment of the variable size vial holder and cap piercer 11. This apparatus comprises a frame 12, an adjustable holder 14, a top plate 16, a cup 18, an extendable and retractable needle 20, and a driver 22 for extending and retracting the needle 20. A multi-lobe cam 22a with associated position switches 24 is used to detect needle position. In addition, a safety switch 24a is used for interlocking the driver with the holder 14 so that the driver 22 cannot extend the needle 20 when a vial 23 is not fully engaged in and held by the holder 14.

In one aspect of the invention, an important feature is provided where the closed end of the vial 23 opposite the capped end trips the safety switch 24a, and that the tongue 34 alone can not enable the needle 20 to extend.

Figure 3:
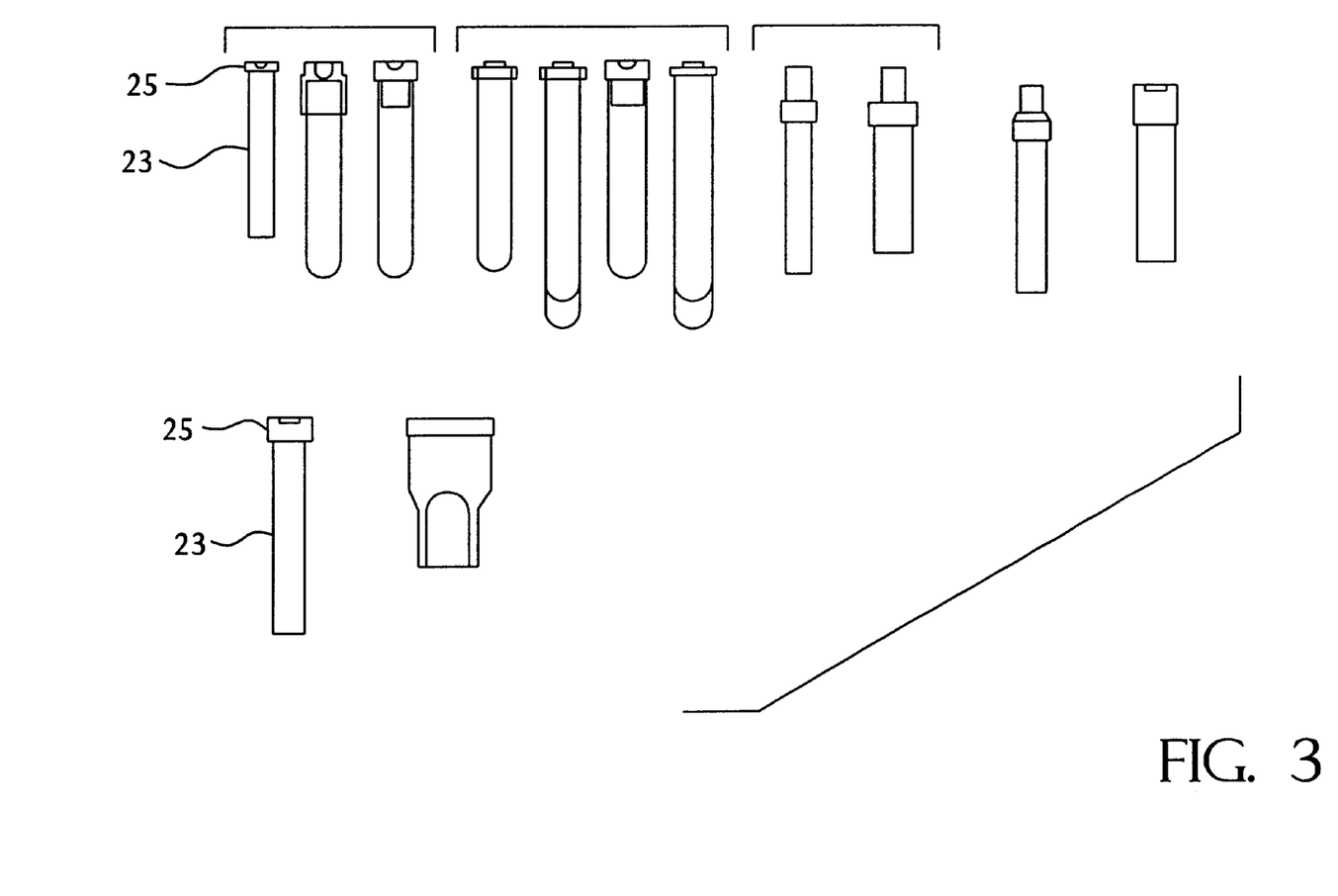
FIG. 3 illustrates various types and sizes of vials sealed with pierceable caps.

The frame 12 in the preferred embodiment includes two ways 26, which are upright members mounted on a base 28. The ways 26 are connected at the top plate 16 by a block 30. The holder 14 is adjustably mounted on the upper end of the frame 12. The cup 18 and the holder 14 is designed to receive and hold a vial 23, also referred to as a tube, such as those shown in FIG. 3. The tubes shown in FIG. 3 range in size from 10.5×64 mm to 16×100 mm. The tubes are sealed with caps 25 which are typically are made of a pierceable material, such as rubber or plastic. The holder 14 is designed to receive and hold the outer surface of a vial or tube 23 opposite the pierceable cap 25 which seals the vial or tube when the cap 25 is seated in the cup 18.

Figure 4:
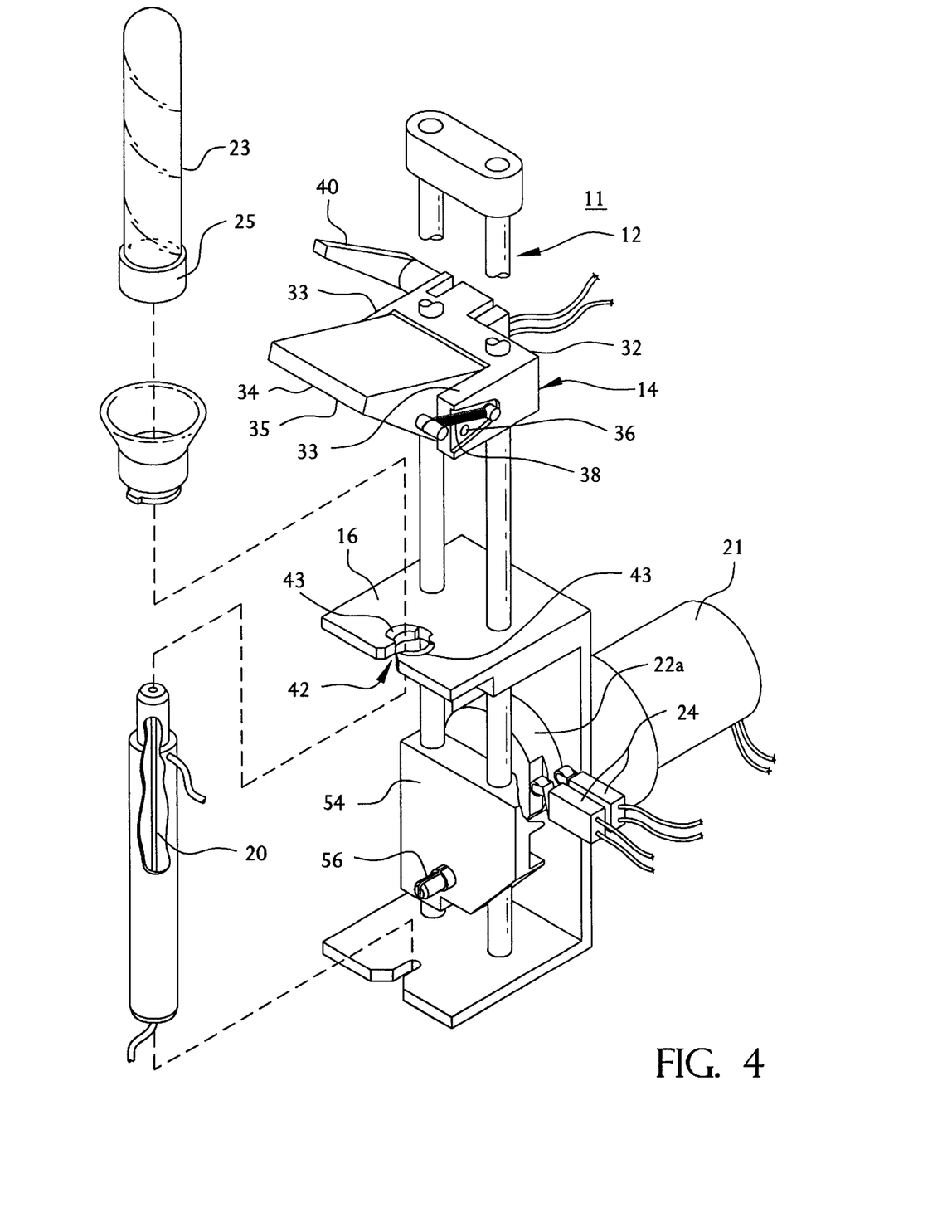
FIG. 4 is an isometric view of a vial holder and cap piercer device illustrating several features of the present invention, including the frame, holder, plate, and driver motor.
Figure 5A:
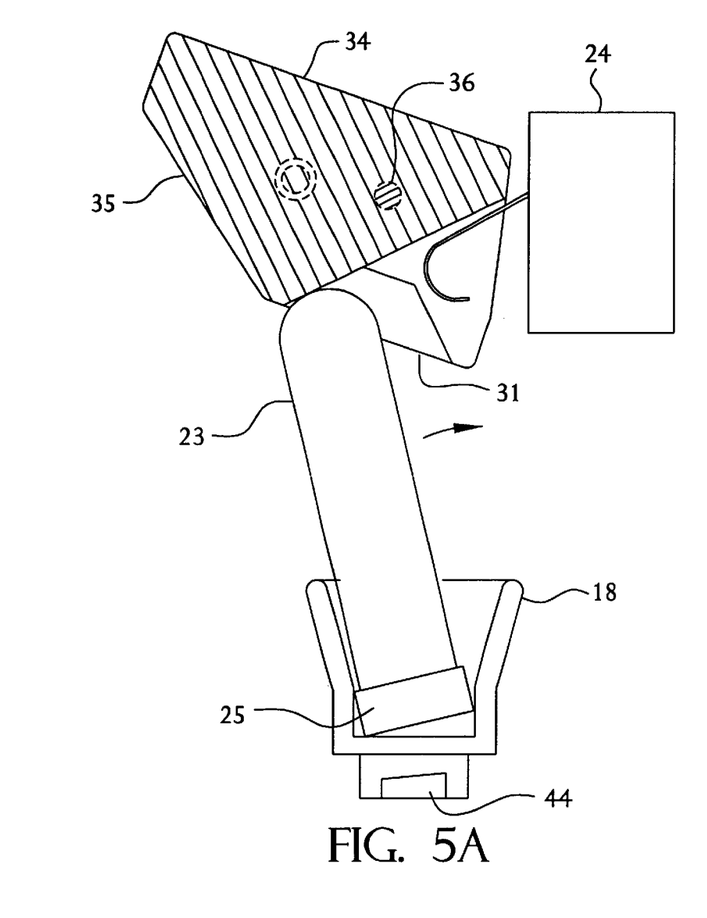
FIG. 5A illustrates a bevel shaped tongue portion of a holder and a recess for receiving and holding a vial according to the present invention.
Figure 5B:
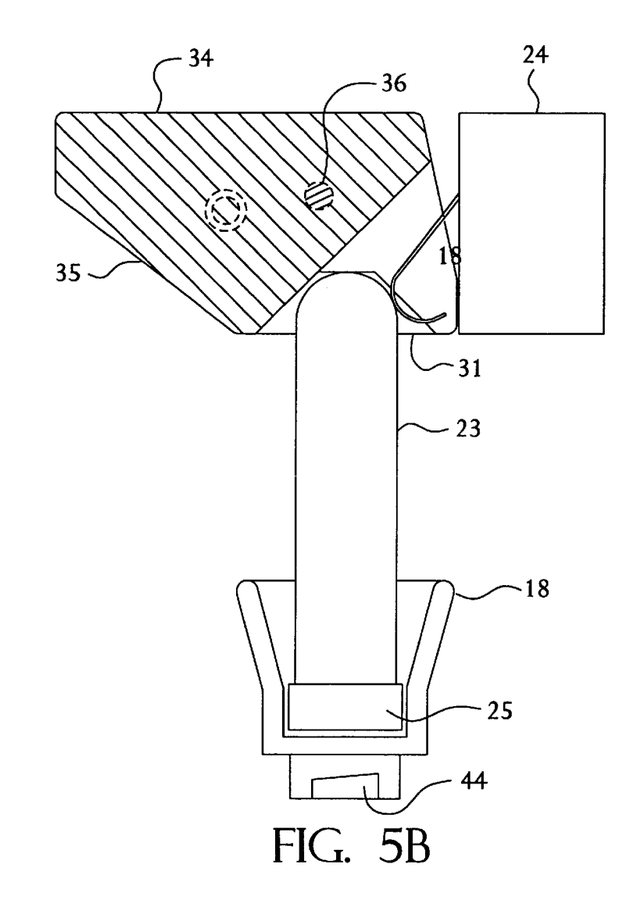
FIG. 5B illustrates a bevel shaped tongue portion of a holder and a recess holding a vial according to the present invention.

In the preferred embodiment, the holder 14 is an over center spring loaded mechanism of the configuration shown in FIG. 4. The holder 14 includes a U-shaped clamp 32 adjustably mounted to the frame 12 and an oblong-shaped tongue 34 mounted between two arms 33 of the clamp 32. The tongue 34 is retained in the clamp 32 by a pin 36 which extends across the width of the clamp 32. The tongue 34 has a beveled surface 35 and pivots about the axis of the pin 36. A spring 38 on one side of the holder 14 biases the tongue 34 in either the closed or open position as shown in FIG. 2 and FIG. 4. The capped end of the vial 23 is inserted into the cup 18 as the vial 23 is pivoted into contact with the tongue 34. The vial 23 is held into position as the tongue 34 pivots into its open and closed position as shown in FIGS. 5A and 5B. The vial 23 is removed from the holder 14 by reversing this process.

As shown in FIG. 5A, the underside of the tongue 34 has a recess 31, also referred to as an indentation, for receiving and holding the outer surface of a vial 23 opposite the pierceable cap 25 which seals the vial 23. When the surface of a vial contacts the beveled surface 35 of the tongue 34, the tongue 34 rotates or flips into the open position as shown in FIG. 5A. Further movement of the vial 23 into the holder causes contact to be made with the recessed 31 portion of the tongue 34. As the vial 23 is pivoted further into the holder 11 the tongue 34 in turn moves into the closed position as shown in FIG. 5B.

In the preferred embodiment, an adjustable handle 40 is mounted on one arm of the U-shaped clamp 32 opposite the spring 38. The adjustable handle 40 is used to reposition the holder 14, which can be moved higher or lower on the frame 12 to adjust for different sizes of tubes or vials. In addition, the adjustable handle 40 may be spring loaded. When the holder 14 is moved to the desired position, it is locked in place. In the preferred embodiment, the adjustable handle 40 lifts and adjusts to 18 detent positions in 360°, so that the angle can be positioned for operator convenience.

Figure 6A:
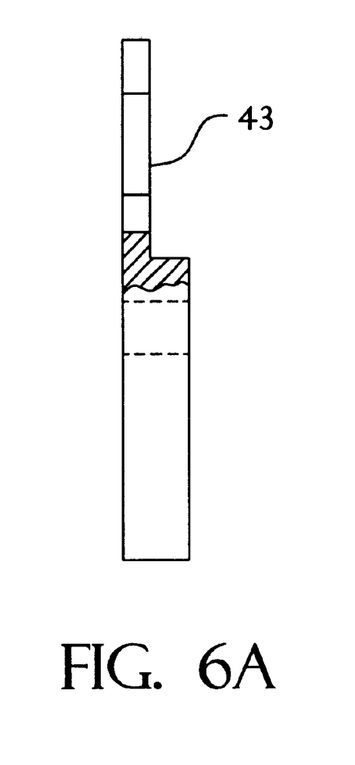
FIGS. 6A illustrate a top view of a plate illustrating keyed openings with bayonet ramps according to the present invention.
Figure 6B:
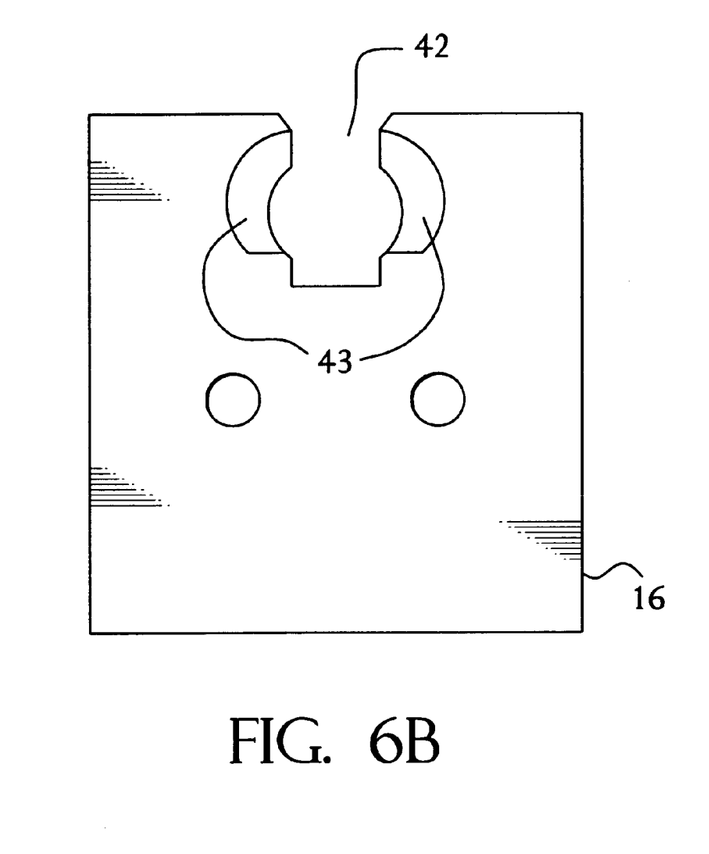
FIGS. 6B illustrate a side view of the plate illustrated in FIG. 6A.
Figure 7A:
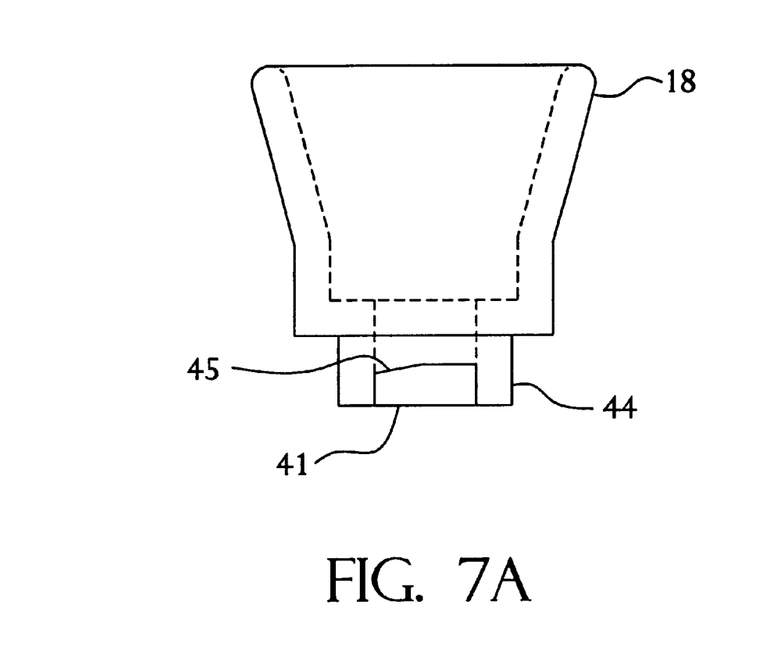
FIG. 7A illustrates a cup with locking device according to the present invention.

Referring to FIGS. 4 and 5, a plate 16 is mounted on the frame 12 and below the holder 14. In the preferred embodiment, the plate 16 has a keyed opening 42 with bayonet ramps 43 which are shown in FIG. 6. The keyed opening 42 in plate 16 is for receiving the cup 18 which is shown in detail in FIGS. 7A and 7B. The opening 42 engages the cup's 18 locking device 44 which is typically located at the bottom of cup 18. The locking device 44 is inserted in the keyed opening 42 and rotated so that the ramped edges 45 of the locking device 44 lock with the bayonet ramps 43 of the keyed opening 42 of plate 16.

Figure 7B:
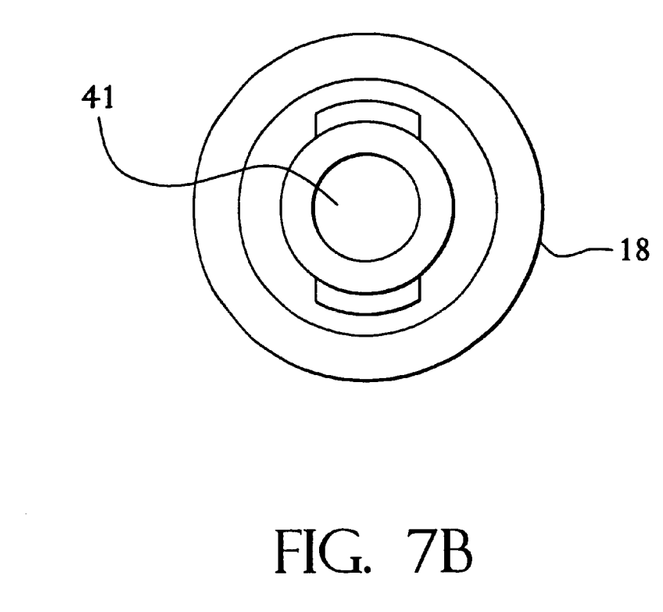
FIG. 7B illustrates a bottom view of the cup shown in FIG. 7A.

Rotation of the cup 18 in the opposite direction unlocks the locking device 44 allowing removal of the cup 18. Different size cups 18 may be mounted on the plate 16 for receiving the pierceable caps 25 on vials 23 like those shown in FIG. 3. It has been found that two different cup sizes are adequate to handle the range of tube sizes shown in FIG. 3. In one aspect, a cup 18 may be used to accept standard size tubes under a 3 milliliter volume, and another cup may be used to accept standard size tubes that are 3 milliliter in volume or greater. The cup 18 has a tapered shape which helps guide a tube or vial into position when placed in the holder 14. In the preferred embodiment, the cup 18 is made of a clear glass-smooth injection molded polycarbonate or acrylic. As shown in FIG. 7B, the bottom of the cup 18 has a small aperture aligned with the hole in plate 16 that allows the needle 20 to pierce the cap 25 of a vial.

Figure 8A:
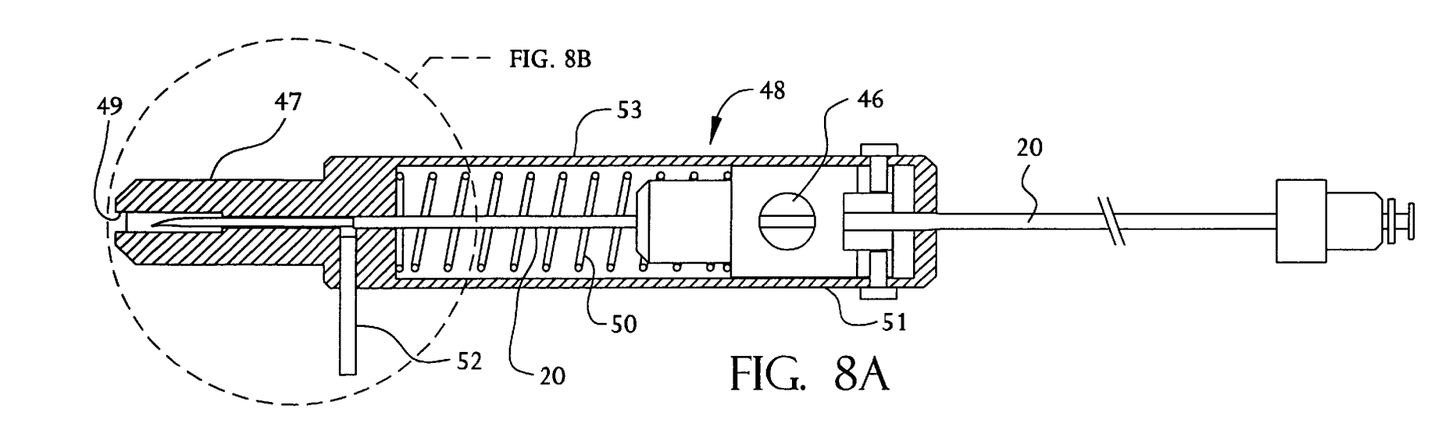
FIG. 8A illustrates a needle and hub assembly according to the present invention in a retracted position.
Figure 9A:
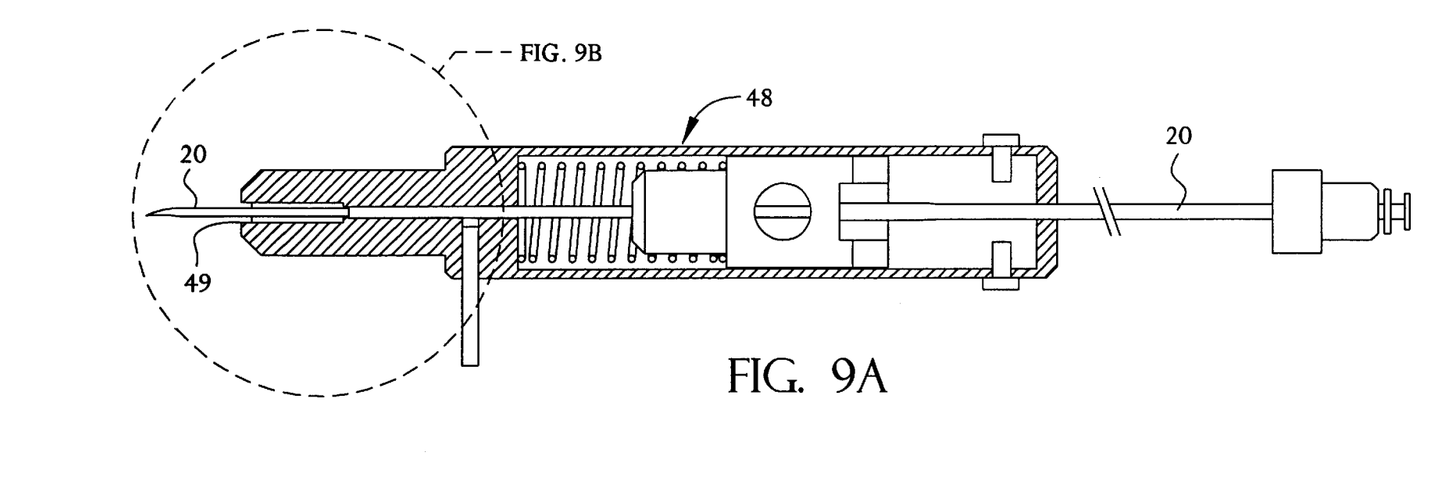
FIG. 9A illustrates a needle and hub assembly according to the present invention in an extended position.

In the invention includes a needle cartridge assembly 48 as shown in FIG. 8A. The needle cartridge assembly 48 includes a needle 20, and a needle cartridge body 53 with a stepped nosepiece 47 and a needle cartridge assembly 48. The needle 20 is attached to a hub assembly 46 that moves within the needle cartridge assembly 48. The needle 20 is extendable and retractable through apertures 41, 42 which are located in the top plate 16 and the cup 18 respectively. Referring to FIG. 9A, the needle 20 may be extended to pierce the cap 25 of the vial 23 that is held by the holder 14. The needle 20 is extended so that the needle 20 may communicate with the contents of the vial 23.

As shown in FIGS. 8A and 9A, the needle hub assembly 46 is mounted within a needle cartridge assembly 48 which is positioned below plate 16. The needle cartridge assembly 48 has a lower end 51, a body 53, and an upper end 47, the top of which has an aperture 49 aligned with the aperture 42 in plate 16. The body 53 of the needle cartridge assembly 48 contains the needle 20 and a biasing means 50 for engaging the needle 20. The biasing means 50 applies a bias to the needle 20 retracting it away from the pierceable cap 25 of the vial 23. In addition, needle cartridge assembly 48 can be removable from the holder 14.

As a safety feature, the biasing means 50 will retract the needle into the needle cartridge assembly 48 whenever the cartridge assembly 48 is removed from the holder 14. In one aspect of the invention, the biasing means 50 may be a coil compression spring.

Figure 9B:
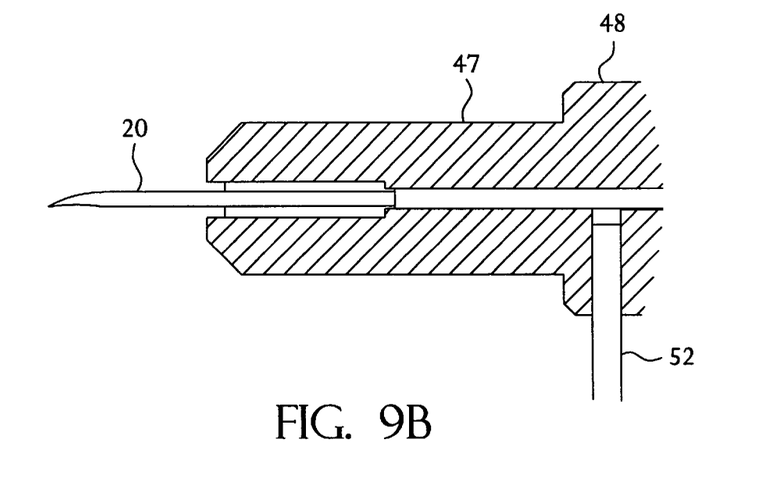
FIG. 9B illustrates the front portion of the needle and hub assembly shown in FIG. 9A.
Figure 10:
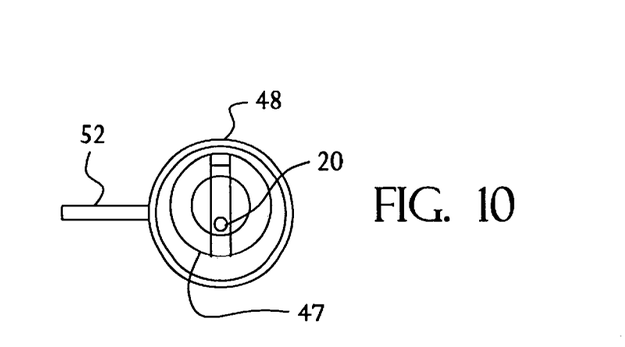
FIG. 10 illustrates eccentric positioning of a needle cartridge assembly according to the present invention.

In one aspect of the invention as shown in FIG. 10, the needle 20 is positioned concentrically with respect to the needle cartridge assembly 48, but eccentrically with respect to the center longitudinal axis of the vial 23 and its cap 25. As an example, in FIG. 9B the nosepiece 47 is shown to be made eccentric with needle cartridge assembly 48. This design allows the needle 20 to extend and retract eccentrically with respect to the center axis of the cap 25. This feature prevents the pierceable caps 25 of the vials 23 to be pierced in the same location, typically the center of the vial's cap 25 when multiple samples are taken from the same vial. After the cap 23 has been pierced and a sample drawn the needle 20 is retracted.

In order to extract a precise amount of sample a circuit is formed by the sample which is conductive, the needle 20 which is conductive, and a second electrode (not shown) located at a fixed distance from the needle in and along a confined path formed by the sample as it is drawn from the vial 23. The sample may be drawn through a non-conductive tube made of plastic or rubber. As the sample is drawn from the vial 23 through the needle 20 the sample comes in contact with the second electrode to form a closed circuit between the conductive needle and the other second electrode. The closed conductive path is used to indicate that a precise amount of sample has been drawn.

In one example, a current can be applied to the needle through pin 56 and carried by the fluid to the electrode down stream. When the current reaches the electrode it can be used to indicate that a sufficient amount of fluid has been drawn and/or that the needle 20 should be withdrawn. As the needle 20 is withdrawn its outer surface is cleaned by a squeegee effect produced by the material of pierceable cap 23 which is typically made of rubber or plastic.

Figure 8B:
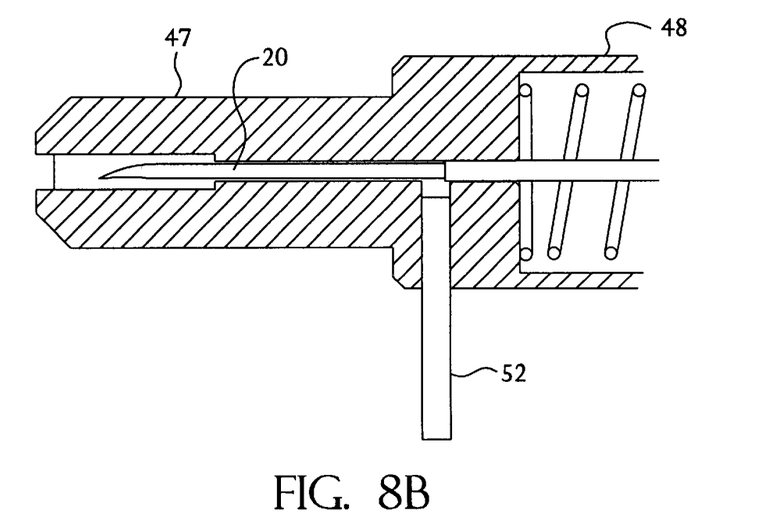
FIG. 8B illustrates the front portion of the needle and hub assembly shown in FIG. 8A.

Referring to FIGS. 8B and 9B, a rinse system is used to clean the inside of the needle 20. In the preferred embodiment, the needle cartridge assembly 48 is connected to a rinse passage 52 for selectively communicating a rinse fluid to the needle 20. The needle 20 may be contained in a chamber within the needle cartridge assembly 48. The chamber is connected to the rinse passage 52 through which the rinse fluid is injected in one direction into the chamber, and from which the rinse fluid is withdrawn in another direction. A first pump (not shown) is used to inject the rinse fluid through the rinse passage 52. A second (not shown) pump is used to withdraw the rinse fluid.

Referring to FIG. 4, movement of the needle 20 is controlled by a driver 22 which causes the needle 20 to extend and retract. In a preferred embodiment the driver 22 includes an electric motor 21. The motor 21 has a shaft that is connected to a scotch yoke mechanism 54, which translates rotary motion to linear motion. Needle 20 rides on a pin 56 connected to the scotch yoke mechanism 54 causing the needle 20 to move up or down during operation. Movement of the needle 20 is controlled by electric circuitry illustrated in FIG. 2A. Switches 24 are used to control the piercing and retracting strokes of the needle 20.

Figure 2A:
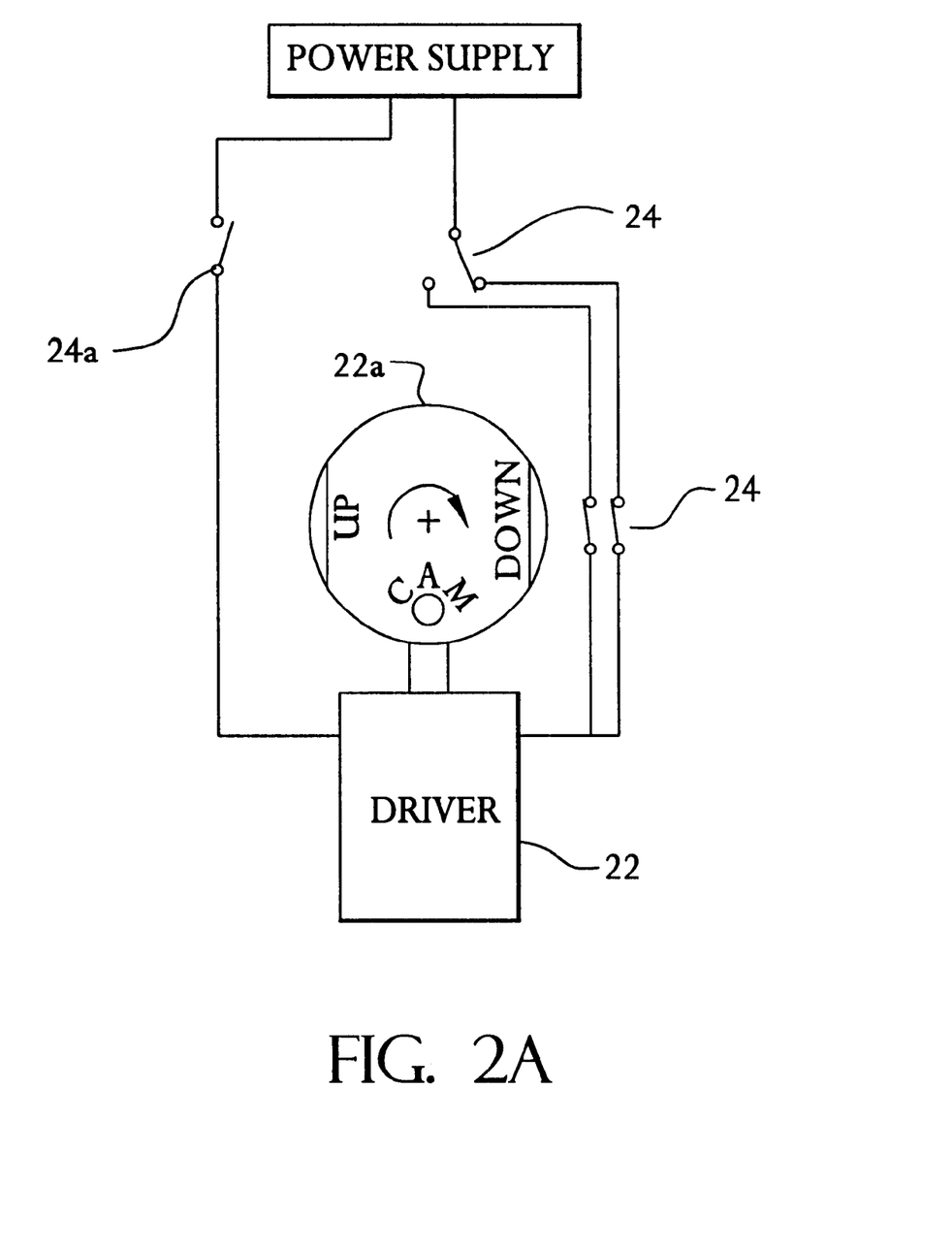
FIG. 2A is a schematic diagram of the electric controls of the vial holder and cap piercer device of FIG. 2.

For example, to indicate needle position, one switch is open when the needle 20 is fully retracted, while another switch is open when the needle 20 is fully extended. A safety switch 24a interlocks the driver 22 with holder 14. When the tongue 34 of the holder 14 is in the open position, safety switch 24a is open, and needle 20 cannot be extended through the aperture in cup 18. When a vial or tube is placed in holder 14 and the tongue 34 moves to the closed position, switch 24a closes, allowing driver 22 to extend the needle 20 to pierce the pierceable cap of the vial.

Prior to running samples, the operator should adjust the height of the holder 14 to fit the size of the vials to be tested. The operator loosens the clamp handle 40, allowing the holder 14 to slide on the ways 26 and moves the holder 14 upward or downward. A vial is then placed in the cup 18 (cap end down). The opposite end of the vial is positioned in the holder 14 until the interlock switch 24a is tripped. The spring applying a bias off the center axis of the tongue 34 keeps it in either an open or closed position in the holder 14.

After inserting the cap end of a vial or tube in the cup 18, the operator pivots the opposite end of the vial or tube into the holder 14. When the tongue 34 is in the open position, the tube or vial first contacts the beveled front of the tongue 34 and kicks it open. With the tongue 34 in the open position the capped end of the vial 23 enters and is engaged by the conical-shaped pocket area of cup 18, and with a pivoting motion is further inserted to close the holder 14. As the closed uncapped end of the vial moves into the recessed portion of the tongue 34 of the holder 14, it trips the recessed interlock switch 24a, which enables the electric motor drive 22 to function. The vial seats securely and stays in position until the needle 20 is fully retracted. The operator may then remove the vial from the holder 14. If an attempt is made to remove the vial 23 from the holder 14 when the cap 25 is being pierced, the interlocking switch 24a will disable the motor drive 22 to prevent injury to the operator by unintended movement of the needle 20.

The present invention may be embodied in other variant forms where the variation does not substantially differentiate from the essential novelty and uniqueness revealed in the foregoing disclosure. Reference should therefore be made to the appendant claims rather than the foregoing specification, as indicating the scope of the invention. It should be understood that many modifications, variations and changes may be made without departing from the spirit and scope of the invention as defined in the claims.

What is claimed is:

1. An automated sample extraction apparatus for automatically withdrawing precise samples of biological fluid from vials of varying sizes sealed with pierceable caps, comprising:

a holder for receiving and holding at least one vial having a pierceable cap sealing said vial;

a cup for receiving the pierceable cap sealing said vial, the bottom of the cup having an aperture aligned with the pierceable cap;

an electrically conductive needle extendable and retractable through the apertures in said cup for piercing the pierceable cap, the needle being hollow to permit a sample of fluid in said vial to be withdrawn through the needle;

a driver for extending and retracting said needle, the driver including a circuit for extracting a precise amount of sample from the vial along a confined path, said circuit comprising said sample, which is conductive, the needle forming a first electrode of the circuit, and a second electrode located a fixed distance from the needle along said confined path so that as the sample is drawn from the vial through the needle the fluid comes in contact with the second electrode to form a closed conductive path between the needle and the second electrode, wherein completion of the conductive path indicates a precise amount of sample has been drawn and terminates extraction of fluid; and a safety switch interlocking said driver with said holder such that said driver can extend said needle through the aperture in said cap only when the vial is held by the holder.

2. The apparatus of claim 1, wherein the holder comprises a U-shaped member, a tongue having a body with a beveled surface and a recess for receiving and holding the outer surface of said vial, the body being pivotally engaged with the U shaped member, and a spring connected to the tongue and the U-shaped member on one side of the holder for biasing the tongue in a closed position when said vial is engaged by the holder.

3. The apparatus of claim 1, further comprising:

said needle being contained in a needle cartridge assembly, said needle cartridge assembly having a lower end, a body, and an upper end, the top of said upper end having an aperture aligned with the aperture in the cup; and a biasing means within the body of said needle cartridge assembly for engaging said needle and biasing the needle away from the pierceable cap of the vial.

4. The apparatus of claim 3, further comprising a rinse passage, wherein said needle cartridge assembly is connected to said rinse passage for selectively communicating a rinse fluid to said needle to clean said needle.

5. The apparatus of claim 3, wherein the needle cartridge assembly is removable.

6. The apparatus of claim 5, wherein the needle cartridge assembly is maintained in a retracted position by the biasing means whenever the cartridge is removed from the device.

* * * * *